United States Patent [19]

Batchelor et al.

[11] 4,091,108

[45] May 23, 1978

[54] ANTIALLERGIC PHARMACEUTICAL COMPOSITION AND USE

[75] Inventors: John Frederick Batchelor, Beckenham; John Henry Gorvin, London, both of England

[73] Assignee: Burroughs Wellcome Co., Research Triangle Park, N.C.

[21] Appl. No.: 619,175

[22] Filed: Oct. 3, 1975

Related U.S. Application Data

[62] Division of Ser. No. 394,421, Sep. 5, 1973, abandoned.

[30] Foreign Application Priority Data

Aug. 17, 1973  United Kingdom ............... 38951/73
Sep. 6, 1972  United Kingdom ............... 41434/72

[51] Int. Cl.$^2$ ............... A61K 31/41; A61K 31/38; A61K 31/39; A61K 31/385
[52] U.S. Cl. ............... 424/275; 424/269; 424/276; 424/277
[58] Field of Search ............... 424/275

[56] References Cited

U.S. PATENT DOCUMENTS 2,985,656  5/1951  Weber ............... 260/249
3,642,997  2/1972  Shen et al. ............... 424/250

OTHER PUBLICATIONS

J.A.C.S., vol. 19, 208–212 (1956).
Chemical Abstracts vol. 66, (1967), 18458c; vol. 75, 20353v, (1971).

*Primary Examiner*—Frederick E. Waddell
*Attorney, Agent, or Firm*—Donald Brown

[57] ABSTRACT

Certain tricyclic sulphoxide compounds each of which is substituted in the 1-,2-,3- or 4-position by a carboxyl or (5-tetrazolyl) group and each of which is optionally substituted in the 5-,6-,7- or 8-position by a second carboxyl or (5-tetrazolyl) group or a substituent selected from cyano, halogen, nitro, alkyl, alkoxy, acyl, amino, acylamino, thioalkyl, alkylsulphinyl and alkylsulphonyl, as well as salts, and optionally substituted esters and amides of the carboxyl substituted compounds and alkyl derivatives of the tetrazolyl substituted compounds, are useful for the relief or prophylaxis of allergic conditions.

7 Claims, 16 Drawing Figures

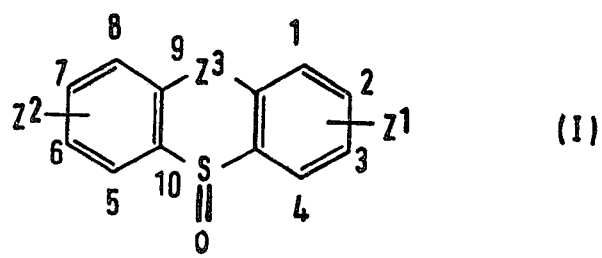
(I)
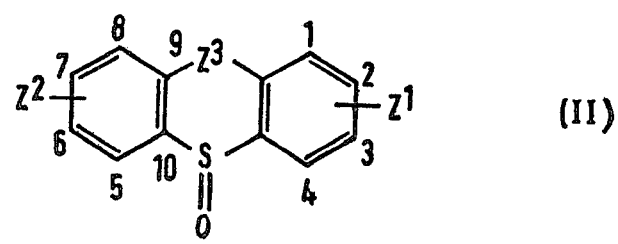
(II)
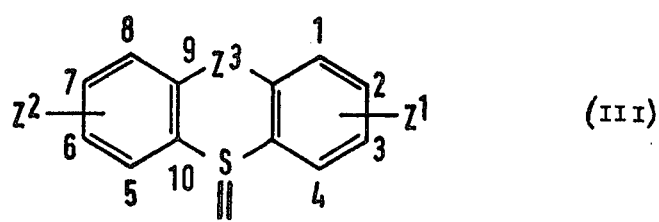
(III)
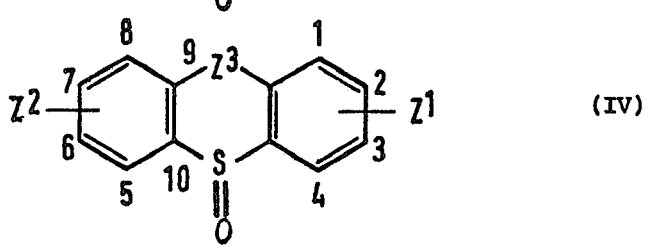
(IV)

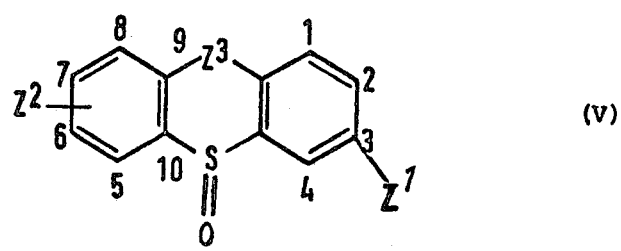
(V)
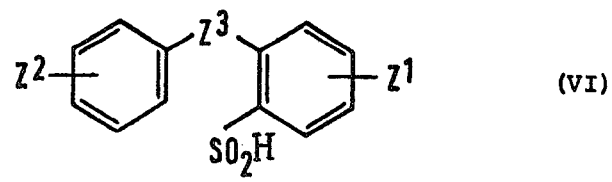
(VI)
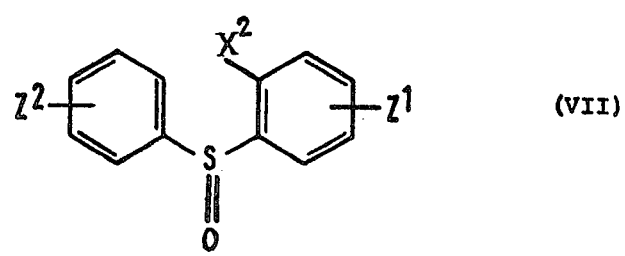
(VII)

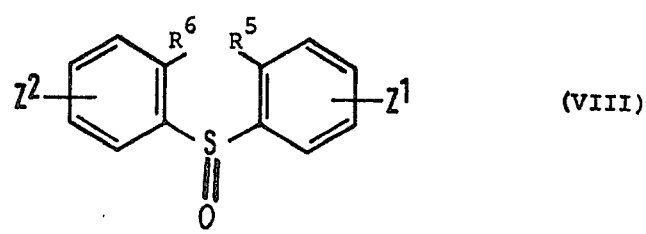
(VIII)
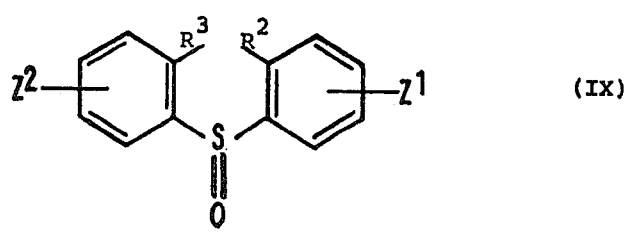
(IX)
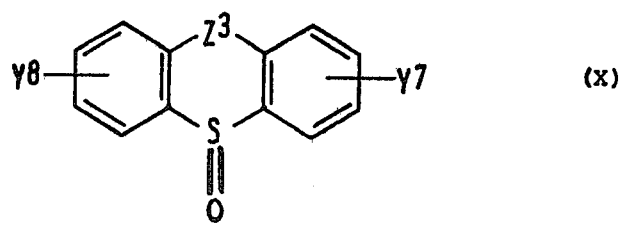
(X)
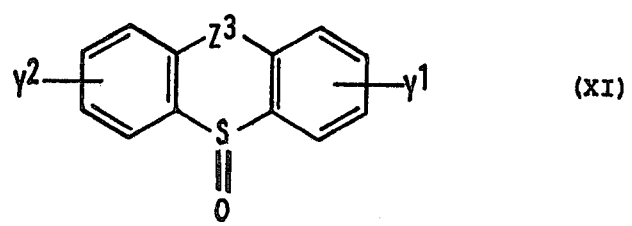
(XI)
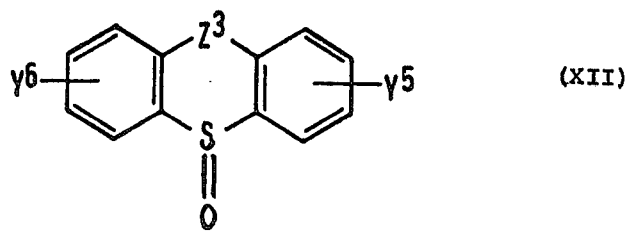
(XII)

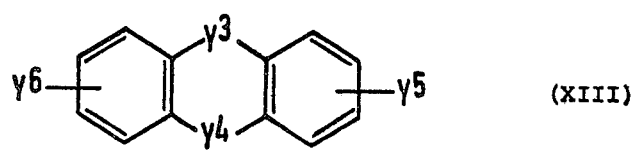
(XIII)
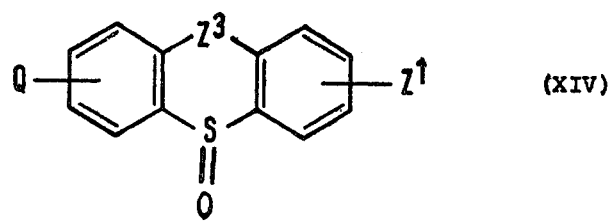
(XIV)
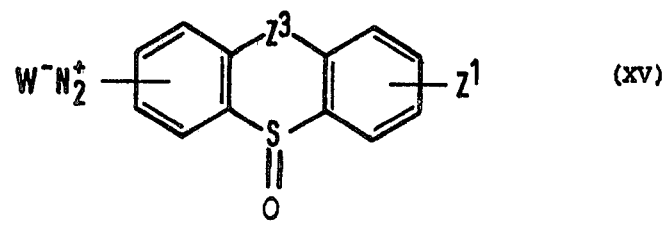
(XV)
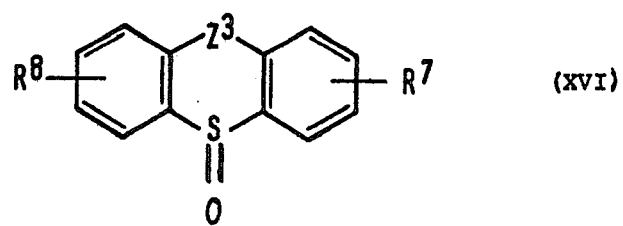
(XVI)

ANTIALLERGIC PHARMACEUTICAL COMPOSITION AND USE

This is a division of application Ser. No. 394,421, filed on Sept. 5, 1973, now abandoned.

The invention relates to tricyclic compounds having medicinal properties, the synthesis of the compounds and their adaptation for medicinal use.

It has been found that tricyclic compounds of formula I, as defined hereinbelow, are active in mammals and in in vitro mammalian preparations as inhibitors of allergic reactions associated with reaginic antibodies of the kind responsible for asthma in man, and that this effect is attributable to the suppression of the release of anaphylactic mediators.

In formula I, $Z^1$ is a substituent in the 1-, 2-, 3-, or 4-position and is carboxyl, 5-tetrazolyl, 5-(1-alkyl) tetrazolyl, or 5-(2-alkyl)tetrazolyl in which the alkyl groups have 1 to 6 carbon atoms and are each optionally substituted by a hydroxyl group or a basic or acidic group; $Z^2$ is hydrogen or a substituent in the 5-, 6-, 7-, or 8-position selected from the values of the group $Z^1$ as defined above or is alkylsulphonyl, alkylsulphinyl, thioalkyl, amino, acylamino, nitro, cyano, halogen preferably chlorine or bromine, acyl, alkyl or alkoxy wherein the "alkyl" moiety of each of the acyl, alkyl, alkoxy, thioalkyl, acylamino, alkylsulphinyl and alkylsulphonyl groups has 1 to 6 carbon atoms; and $Z^3$ represents a bond or is carbonyl, oxygen, sulphur, sulphoxide or methylene;

together with salts of said compounds and when at least one of $Z^1$ and $Z^2$ is a carboxyl group, esters and amides of said compounds.

The inhibition activity of the compounds of formula I has been demonstrated (a) in tests using the response of passive cutaneous anaphylaxis (PCA test) in which is measured the skin reaction produced as the result of interaction between specific antigen injected intravenously and cell-fixed reaginic antibody previously injected into the skin of a mammal (see for example Z. Ovary: Fedn. Proc. Am. Soc. exp. Biol. 24, 94 (1965)), (b) by measurement of the amount of histamine released after antigen challenge of pertioneal mast cells from actively sensitised rats (see for example, 1. Acta Pharmacol. et Toxicol. 30, supp. 1 (1971)), 2. Thorax, 27/1, 38 (1972)), and (c) by measurement of the histamine released from human chopped lung tissue passively sensitised in vitro with reaginic anbitody when challenged with the homologous anitgen (Br. Med. J. 3,272 (1968)). The activity of acids of formula I has been demonstrated as described hereinabove using solutions of the anion.

For the sake of convenience, compounds of formula I wherein either of $Z^1$ and $Z^2$ is or both are an alkyl carboxylate group, are hereinafter referred to as 'esters' of formula I. Similarly references to 'amides' of formula I shall be construed as references to compounds of formula I wherein one or both of $Z^1$ and $Z^2$ is an optionally substituted carboxamide, and references to 'salts' of formula I shall mean salts of formula I wherein one or both of $Z^1$ and $Z^2$ is a salt of the acid.

Pharmaceutically acceptable salts of compounds of formula I include ammonium salts, alkali metal salts such as sodium and potassium salts, alkaline earth salts such as magnesium and calcium salts, and salts of organic bases, for example, amine salts derived from mono-,di-, or tri-lower alkyl or lower alkanolamines such as triethanolamine and diethylaminoethylamine and salts with heterocyclic amines such as piperidine pyridine, piperazine and morpholine. Especially valuable for intravenous and pulmonary administration are water soluble salts, most preferably those having a solubility in water of at least 1 mg/ml.

For the purposes of medicinal administration, the carboxylate salt group may be a salt of any pharmaceutically acceptable cation, since the pharmacological activity of the salts is associated with the anion.

Suitable amides include amides derived from primary or secondary, aliphatic amines such as N-alkyl and N,N-dialkyl amines for example diethylamine. Suitable esters include esters derived from alkyl alcohols. The alkyl moieties of the alkyl esters and N-alkyl and N,N-dialkyl carboxamides, preferably each have 1 to 6 carbon atoms, most desirably 1 to 4 carbon atoms.

Each of the alkyl moieties of the esters and amides is optionally substituted by at least one hydroxy, basic or acidic substituent. Suitable basic substituents include amino groups optionally substituted by one or two alkyl groups and heterocyclic amino groups such as piperidine or morpholine. The esters and amides having basic substituents as well as the amides themselves may be in the form of pharmaceutically acceptable acid addition salts.

Suitable acidic substituents include 5-tetrazolyl groups and carboxyl groups, and their pharmaceutically acceptable salts.

Compounds of formula I wherein $Z^3$ is sulphoxide occur in either of two isomeric forms; cis and trans (see Chickos et al, J. Am. Chem. Soc. 1967, 89, 4815) and may exhibit optical activity. The cis isomers have been found to possess superior inhibition activity compared with the trans isomers as demonstrated in one or more of the tests described hereinbefore.

Include within the scope of compounds of formula I are tricyclic compounds of formula II wherein $Z^1$ is a 5-(1-R) tetrazolyl or 5-(2-R)tetrazolyl group wherein R is an alkyl group having 1 to 6 carbon atoms or a cation, a group $CO_2R$ wherein R has the same meaning as before, or an optionally substituted carboxamide group; $Z^2$ is hydrogen or a substituent selected from a group $Z^1$ as defined hereinbefore, nitro, halo, alkyl, alkoxy, acyl, thioalkyl, amino, acylamino, cyano alkylsulfinyl and alkylsulfonyl wherein the 'alkyl' moiety of the alkyl, alkoxy, acyl, thioalkyl, acylamino, alkylsulfinyl and alkylsulfonyl substituents has 1 to 6 carbon atoms, and $Z^3$ represents a bond or is selected from —O—, —S—, —CH$_2$—, —S(:O)— and —C(:O)—.

Novel compounds of the present invention include tricyclic compounds of formula III wherein $Z^1$ is a 5-(1-R)tetrazolyl or 5-(2-R)tetrazolyl group wherein R is an alkyl group having 1 to 6 carbon atoms or a cation, a group $CO_2R$ wherein R has the same meaning as before, or an optionally substituted carboxamide group;

$Z^3$ represents a bond or is selected from —O—, —S—, —CH$_2$—, —S(:O)—, and —C(:O)—; and $Z^2$ is hydrogen when:

(a) $Z^3$ is —(C:O)—, a bond or —CH$_2$— and $Z^1$ is as defined above;

(b) $Z^3$ is —S(:O)— or —S— or is —O— and $Z^1$ is carboxyl in the 3- or 3- or 2-position, respectively; or (c) $Z^3$ is as first defined above and $Z^1$ is a group $CO_2R$ as first defined hereinabove provided that when $Z^3$ is —S(:O)—

$Z^1$ is not ethyl carboxylate, 5-(1-R) tetrazolyl or 5-(2-R) tetrazolyl as first defined hereinabove; or $Z^2$ is carboxyl when $Z^3$ is not —S—; or $Z^2$ is a substituent selected from nitro, halo, alkyl, alkoxy, acyl, amino, acylamino, thioalkyl, cyano, alkylsulfinyl and alkylsulfonyl wherein the 'alkyl' moiety of the alkyl, alkoxy, acyl, thioalkyl, acylamino, alkylsulfinyl and alkylsulfonyl substituents has 1 to 6 carbon atoms.

Compounds of formula I which show a very high antiallergic activity include 3-carboxythioxanthone-10-oxide, and 3,7-phenoxathiin-10-oxide dicarboxylic acid, and salts of these compounds, especially alkali metal salts including sodium and potassium salts.

Novel compounds of the present invention include tricyclic compounds of formula (IV) wherein $Z^1$ is a substituent in the 1-,2-,3-, or 4-position and is carboxyl, 5-tetrazolyl, 5-(1-alkyl)tetrazolyl, or 5-(2-alkyl)tetrazolyl in which the alkyl groups have 1 to 6 carbon atoms and are each optionally substituted by a hydroxyl group or a basic or acidic group;

$Z^3$ represents a bond or is carbonyl, oxygen, sulphur, sulphoxide or methylene; and $Z^2$ is hydrogen when:

(a) $Z^3$ is carbonyl, a bond or methylene and $Z^1$ is as defined above;

(b) $Z^3$ is sulphoxide or sulphur or is oxygen and (c) 1 is carboxyl in the 3- or 3- or 2-position, respectively; or c) $Z^3$ is as first defined above and $Z^1$ is a carboxylate salt group, an alkyl carboxylate group having 1 to 6, preferably 1 to 4 carbon atoms, provided that when $Z^3$ is sulphoxide $Z^1$ is not ethyl carboxylate, 5-tetrazolyl, 5-(1-alkyl)tetrazolyl or 5-(2-alkyl)tetrazolyl in which the alkyl groups have 1 to 6 carbon atoms and are each optionally substituted by a hydroxyl group or a basic or acidic group; or $Z^2$ is carboxyl when $Z^3$ is not sulphur; or $Z^2$ is a substituent in the 5-6-,7-, or 8-position and is selected from alkylsulphonyl, alkylsulphinyl, acylamino, thioalkyl, amino, nitro, cyano, halogen, preferably chlorine or bromine, acyl, alkyl, or alkoxy wherein the "alkyl" moiety of each of the acyl, alkyl, alkoxy, thioalkyl, acylamino, alkylsulphinyl and alkylsulphonyl groups has 1 to 6 carbon atoms; together with salts of said compounds and when at least one of $Z^1$ and $Z^2$ is a carboxyl group, esters or amides thereof, except for 7-nitro-1-carboxythianthrene-5,10-dioxide.

Preferred novel compounds of the present invention include tricyclic compounds of formula V wherein $Z^1$ is a substituent in the 3-position and is carboxyl, a carboxylate salt group, 5-tetrazolyl, or a 5-tetrazolyl salt group;

$Z^2$ is hydrogen or a substituent in the 6- or 7-position selected from the values of the group $Z^1$ as defined above or is alkylsulphonyl, alkylsulphinyl, thioalkyl, amino, acylamino, cyano, nitro, halogen preferably chlorine or bromine, acyl, alkyl or alkoxy wherein the 'alkyl' moiety of each of the acyl, alkyl alkoxy, thioalkyl, acylamino, alkylsulphinyl and alkylsulphonyl groups has 1 to 6 carbon atoms; and $Z^3$ is carbonyl, oxygen or sulphoxide.

The compounds of formula I may be prepared by known chemical techniques. In general, the methods include (a) oxidation of sulphide precursors using specific oxidising agents, (b) cyclisation wherein the central ring is completed by ring closure, and (c) conversion of suitable substituent groups to the required $Z^1$ and $Z^2$ substituent groups by a variety of techniques.

Because of the relative instability of the sulphoxide group to reduction, oxidation, and hydrolysis techniques required for methods (b) and (c) listed above, the preferred technique is oxidation of a sulphide precursor. In general, suitable specific oxidants include iodosobenzene, iodosobenzene diacetate, sodium metaperiodate, hydrogen peroxide in ethanol or acetic acid solutions, organo-peroxy acids such as m-chloroperoxybenzoic acid, nitric acid, and dinitrogen tetroxide. Oxidation may also be effected by treatment with chlorine or bromine in a suitable organic solvent such as carbon tetrachloride, or with an organic chlorinating or brominating agent, for example N-chloro- or N-bromosuccinimide, followed by hydrolysis with water.

It will be appreciated that in the case of the different heterocyclic ring structures, different oxidants may be particularly preferred. For example thioxanthones (formula I, $Z^3$ = carbonyl) were found to be oxidised preferably by iodosobenzene diacetate, thioxanthenes (formula I, $Z^3$ = methylene) by m-chloroperoxybenxoic acid, and phenoxathiins (formula I, $Z^3$ = oxygen) by hydrogen peroxide or nitric acid.

Cyclisation methods may include either formation of the sulphoxide from an acyclic sulphinic acid of formula VI or the formation of the $Z^3$ bridge by a variety of methods.

Suitable methods of cyclising sulphinic acid compounds of formula VI, wherein $Z^3$ is, oxygen, sulphur or methylene, include heating with a dehydrating protonic acid such as sulphuric acid or polyphosphoric acid at a temperature preferably from 25° to 150° C. It will be appreciated that the stability of the sulphoxide group in the precursor or product may determine the upper temperature limit, and that if $Z^2$ is a highly deactivating substituent cyclisation with retention of the sulphoxide group may be precluded.

Formation of the $Z^3$ bridge may be carried out in certain cases by cyclisation of a compound of formula VII wherein $Z^1$ and $Z^2$ have the meaning defined in formula I, provided that $Z^2$ is not a deactivating substituent. Thioxanthones of formula I (wherein $Z^3$ is a carbonyl group) may thus be formed from compounds of formula VII wherein $X^2$ is a carboxylic acid group or derivative such as cyano, alkyl carboxylate, optionally subsituted carbamoyl or acyl halide. Thioxanthenes of formula I (wherein $Z^3$ is a methylene group) may similarly be formed from compounds of formula VII wherein $X^2$ is a group —$CH_2O'$, $O'$ being a suitable leaving group such as hydroxyl, alkyl or aryl sulphonyl, or halo. In each case cyclisation may be affected by treating the precursor of formula VII with a Lewis acid, such as aluminium chloride or boron trifluoride, or protonic acid, such as sulphuric acid or polyphosphoric acid, optionally in the presence of a non-polar solvent, at temperatures preferably from 25° to 150° C. It will be appreciated that the reaction conditions will be dependent on the stability of the sulphoxide precursor and product to those conditions.

Formation of the $Z^3$ bridge where $Z^3$ is sulphur to give thianthrene oxides, may be carried out by reacting a compound of formula VIII, wherein $Z^1$ and $Z^2$ are defined in formula I and $R^5$ and $R^6$ are the same or different and are leaving groups such as halo or nitro, with an inorganic sulphide such as sodium sulphide.

Formation of the $Z^3$ bridge where $Z^3$ is sulphur or oxygen (to give thianthrene or phenoxathiin, oxides) may be effected by cyclisation of a compound of formula IX wherein one of $R^2$ and $R^3$ is a leaving group such as halo or nitro and the other is a thiolate anion, or precursor yielding thiolate anion in a basic medium, for example thiol or thioxanthante, or is a hydroxy group or precursor thereof, respectively. Such cyclisations may be advantageously carried out in a polar aprotic solvent such as dimethylformamide, N-methyl-2-pyrrolidone or sulpholane at temperatures up to 150° C. Other solvents, such as water or ethanol, may also be used.

Modification of the $Z^3$ bridge may be brought about by oxidation or reduction in certain cases. For example thioxanthenes (wherein $Z^3$ is methylene), may be oxidised to thioxanthones (wherein $Z^3$ is carbonyl) by dissolving the methylene precursor in a basic solvent such as pyridine, containing a strong base catalyst such as triton B, and passing air through the solution. Similarly thianthrenes and thianthrene-5-oxides (wherein $Z^3$ is sulphur) may be oxidised to thianthrene-5,10-dioxides (wherein $Z^3$ is sulphoxide) by a suitable oxidising agent such as hydrogen peroxide or m-chloroperoxybenzoic acid. In this context it may be noted that certain oxidants specifically produce one or other of the geometric isomers. For example, oxidation using chlorine results in the formation of cis-thianthrene-5,10-dioxides whilst oxidation using peroxides results in the formation of trans-thianthrene-5,10-dioxides. It may also be noted that cis-thianthrene-5-10-dioxides of formula I may be prepared from the corresponding trans isomers by thermal isomerisation at a temperature of the order of 280° C.

Alternatively thianthrene-5,10-dioxides may be reduced to thianthrene-5-oxides, by heating with strong acids such as sulphuric or hydrochloric acid, or with thionyl chloride.

In formula I wherein one or both of $Z^1$ and $Z^2$ are tetrazolyl or (1-alkyl)tetrazolyl groups, these compounds may be prepared by reaction of hydrazoic acid or a salt thereof or nitrous acid with an appropriate compound of formula X wherein $Y^7$ is a group $Z^1$ as defined in formula I or a tetrazolyl group precursor and $Y^8$ is a group $Z^2$ as defined in formula (I) or a tetrazolyl group precursor, provided that at least one of $Y^7$ and $Y^8$ is a tetrazolyl group precursor.

When hydrazoic acid or a salt thereof is used, a suitable tetrazolyl group precursor is a group

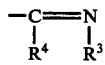

wherein $R^3$ and $R^4$ together form a bond (nitrile), $R^3$ is hydrogen or alkyl amd $R^4$ is alkoxy having 1 to 6 carbon atoms (imidoester), thioalkyl having 1 to 6 carbon atoms (imidothioester), —NH—NH$_2$ (amidrazone), or amino (amidine) or $R^3$ is hydroxy and $R^4$ is amino (amidoxime), or $R^3$ is alkyl and $R^4$ is halogen (imidohalide). In the case of amidoximes and nitriles, only tetrazolyl compounds may be produced and in the case of imidohalides only alkyltetrazolyl compounds may be produced. The reaction is preferably carried out in a polar aprotic liquid medium using a salt of hydrazoic acid.

When nitrous acid is used a suitable tetrazolyl precursor group is a group

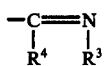

wherein $R^3$ is hydrogen or alkyl and $R^4$ is —NH—NH$_2$ (amidrazone).

The tetrazolyl compounds of formula I thus prepared may be isolated as the free acid or as a tetrazolyl salt, and the one converted to the other in known manner and as specifically described below in relation to the carboxylic acids of formula I and their salts.

The 5-(1- and 2-alkyl)tetrazolyl compounds of formula I may be made from the corresponding tetrazolyl compounds of formula I or their salts by alkylation.

The carboxylic acids of formula I, wherein one or both of $Z^1$ and $Z^2$ are carboxyl may be prepared by a variety of methods which include as the final step the formation of the carboxyl group. These compounds may be isolated as the free acid, as salts thereof, or converted to amides or esters of formula I, depending upon the nature of the desired products. Thus they may be prepared by hydrolysis of a compound of formula XI wherein at least one of $Y^1$ and $Y^2$ is a carboxyl group precursor, such as a nitrile group, trichloromethyl group or a group COL$^1$ wherein L$^1$ is a leaving group, such as a nucleophilic atom or group, for example, a trichloromethyl group, an optionally substituted amino group, a halogen atom or an alkoxy group, when the other is $Z^1$ or $Z^2$ as defined in formula I, as appropriate, or is $Y^1$ as defined above; and $Z^3$ has the meaning defined in formula I. Hydrolysis may be effected heating a compound of formula XI with water, a base or a dilute aqueous mineral acid optionally with an organic acid provided conditions are chosen so as to minimise modification of the sulphoxide bridge(s). For example, one may use dilute sulphuric acid or dilute hydrochloric acid with acetic acid, or a base such as an aqueous alkali metal hydroxide or alkoxide.

By means of nucleophilic substitution reactions analogous to hydrolysis, for example, alcoholysis and ammonolysis, esters and amides of formula I may be prepared directly from compounds of formula XI. Thus reaction of a compound of formula XI with an appropriate alcohol yields an ester of formula I, and reaction with ammonia or an appropriate primary or secondary amine yields an amide of formula I.

The carboxylic acids of formula I and their salts may also be made by oxidation of a compound of formula XII wherein $Y^5$ is an acyl group or a group $Z^1$ as defined in formula I, $Z^3$ is as defined in formula I, and $Y^6$ is an acyl group or a group $Z^2$ as defined in formula I provided that at least one of $Y^5$ and $Y^6$ is an acyl group.

Oxidation of compounds wherein $Z^1$ and/or $Z^2$ is acyl may be effected with such conventonal oxidising agents as nitric acid, or aqueous solutions of salts of hydrochlorous and hypobromous acids in the presence of a base. These oxidation procedures are advantageously effected with heating in the liquid phase. The reaction conditions are chosen to minimise oxidation of the sulphur of the tricyclic nucleus.

If desired, oxidative formation of $Z^1$ and/or $Z^2$ carboxyl groups, the bridging sulphoxide linkage, and $Z^3$ sulphoxide or carbonyl linkage, may be carried out either simultaneously or sequentially. Thus compounds of formula I may be prepared by oxidation with an appropriate oxidising agent of a compound of formula XIII wherein $Y^5$ and $Y^6$ are as defined above in formula XII, $Y^3$ represents a bond or is carbonyl, oxygen, sulphur, sulphoxide, or methylene and $Y^4$ is sulphur or sulphoxide provided that at least one of $Y^3$, $Y^4$, $Y^5$ and $Y^6$ is not the same as $Z^3$, sulphoxide, $Z^1$ and $Z^2$ respectively as defined in formula I but is an oxidisable atom or group as defined in this formula.

The compounds of formula I wherein $Z^2$ is other than hydrogen, alkyl, acyl, carboxyl or a derivative thereof or tetrazolyl or a derivative thereof may also be made by formation of the group $Z^2$ as the final step. Such compounds are prepared by introducing an alkylsulphonyl group, alkylsulphinyl group, cyano group, halogen, amino group, acylamino group, nitro group, cyano group, halogen atom or alkoxy group into an appropriate compound of formula XIV wherein $Z^1$ and $Z^3$ are as defined in formula I and O is hydrogen, a leaving group or a precursor, by known methods.

Thus where $Z^2$ is amino, the compounds may be made by reduction of the corresponding nitro compounds which themselves may be made by nitration. The amino compounds may be converted into acylamino compounds by acylation and into the corresponding diazonium compounds of formula XV wherein $Z^1$ and $Z^3$ are defined in formula I and W is an anion, for example chloride, bromide or hydrogen sulphate by reaction with nitrous acid. These diazonium compounds may be converted by known methods to the alkoxy compounds (by reaction with water and alkylation of the resulting hydroxy compounds); to the halo compounds (by the Sandmeyer reaction using cuprous bromide or chloride; by the Gattermann reaction using a copper catalyst to produce bromo or chloro compound where W is the chloride or bromide ion; by the Balz-Schiemann reaction using the fluoroborate diazonium salt to produce the fluoro compounds; or by using an alkali metal iodide to produce the iodo compounds); to the nitrile compounds (by modified Sandmeyer of Gattermann reactions using cuprous cyanide or potassium cyanide and copper powder); to thiols and alkylthio compounds (by the Leuckart synthesis by formation of diazoxanthates or diazothioxanthates from the diazo compounds and alkali metal alkyl xanthates or thioxanthates respectively which are decomposed in faintly acid cuprous media to the alkylthio compounds and to thiols on hydrolysis). The thiols may if desired by alkylated to the alkylthio compounds of formula I, and these in turn oxidised to alkylsulphinyl compounds of formula I.

It will of course be understood that the oxidative formation of the side chains $Z^1$ and/or $Z^2$, the bridging carbonyl and sulphoxide groups $Z^3$ and the bridging sulphoxide linkage, may be carried out either simultaneously as a one-pot reaction or sequentially, by the use of appropriate oxidising agents.

In the operation of the foregoing synthetic methods, it will also be understood that where the groups $Z^1$ and $Z^2$ are formed prior to the complete formation of the desired compound, then in some instances $Z^1$ and/or $Z^2$ must be protected from inter-reaction in the final synthetic stage or stages. In other instances it is advisable to form the groups $Z^1$ and/or $Z^2$ as the final synthetic step, if the group(s) would react in the final synthetic stage(s).

Pharmaceutically acceptable salts of tetrazoles or carboxylic acids of formula I are prepared by any conventional method, for example, by neutralising the corresponding carboxylic and or tetrazole with an appropriate Bronsted base, or by double decomposition of a salt of an acid or tetrazole of formula I so as to produce the desired salt of an appropriate pharmaceutically acceptable cation. The carboxylic acid or tetrazole may be either the isolated acid or tetrazole, or may be present in solution in the reaction mixture resulting from a preparation of the compound, for example by such a method as described hereinbefore. Suitable Bronsted bases include organic bases such as ethanolamine, and bases containing ammonium, and alkali metal and alkaline earth metal cations.

Salts of formula I may be isolated from a reaction medium by any conventional process for the isolation of salts from a solution thereof in a polar medium.

Desirably the salts of formula I are purified prior to incorporation in a pharmaceutical composition by any conventional method.

Esters and amides of acids of formula I may be prepared by any conventional method including esterification of the acid or acid chloride with an alkyl or aryl alcohol to yield the corresponding alkyl or aryl ester respectively and reaction of the acid or acid chloride with ammonia or an amine to yield the corresponding amine or substituted amide respectively. Compounds of formula I where $Z^1$ and $Z^2$ are different and are chosen from acid, ester, amide and salt functions, may be prepared by the above methods, and by partial hydrolysis, where appropriate.

The compounds of formula I are useful in the treatment or prophylaxis of mammalian allergic conditions such as asthma and other allergic chest conditions, hay fever (allergic rhinitis), conjunctivitis, urticaria and eczema. In particular they are of value in reaginic mediated Type I hypersensitivity asthma ('extrinsic asthma') and the so-called 'intrinsic asthma' in which no sensitivity to extrinsic antigen can be shown.

The magnitude of a prophylactic or therapeutic dose of compound of formula I will of course vary with the nature of the severity of the allergic condition to be treated and with the particular compound of formula I and its route of administration. In general the dose range lies within the range of 2 $\mu$g. to 100 mg. per Kg. body weight of a mammal.

In the case of an allergic condition as defined hereinbefore, for example, allergic asthma, a suitable dosage is from 20 $\mu$g. to 0.5 mg., for example about 0.1 to 0.5 mg., of a compound of formula I, per Kg. of bodyweight of the patient undergoing treatment, when pulmonary administration as described hereinafter is employed. In the case where a composition for intravenous administration is employed a suitable dosage range is from 0.2 to 10 mg. (preferably 1 to 5 mg.) of a compound of formula I per Kg. of bodyweight of patient, and in the case where an oral composition is employed a suitable dosage range is from 1 to 50 mg. of a compound of formula I per Kg. of bodyweight of a patient, preferably from 10 to 40 mg/Kg.

In the case where a composition for nasal and ocular administration is employed, for example, in the treatment of allergic rhinitis, a suitable dose is from 0.5 to 25 mg. of a compound of formula I per patient.

The pharmaceutical compositions of the present invention comprise a compound of formula I as an active ingredient, and may also contain pharmaceutically acceptable carrier and optionally other therapeutic ingredients. The compositions include compositions suitable for oral, rectal, opthalmic, pulmonary, nasal, dermal, topical, or parenteral (including subcutaneous, intramuscular and intravenous) administration, although the most suitable route in any given case will depend on the nature and severity of the condition being treated, and on the nature of the active ingredient. They may be conveniently presented in unit dosage form and prepared by any of the methods well known in the art of pharmacy.

Pharmaceutical compositions of the present invention suitable for oral administration may be presented as discrete units such as capsules, cachets or tablets each containing a predetermined amount of the active ingredient; as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more accessory ingredients.

Desirably, each discrete unit contains from 50 mg. to 500 mg. of the active ingredient.

A valuable form of a pharmaceutical composition of the present invention, for use in the treatment of allergic asthma, is one suitable for pulmonary administration via the buccal cavity. Preferably the composition is such that particles having a diameter of 0.5 to 7$\mu$, most preferably 1 to 6$\mu$, containing active ingredient, are delivered into lungs of a patient. Such compositions are conveniently in the form of dry powders for administration from a powder inhalation device or self-propelling powder-dispensing containers; preferably the powders comprise particles containing active ingredient of which particles at least 98% by weight have a diameter greater than 0.5$\mu$ and at least 95% by number have a diameter less than 7$\mu$. Most desirably at least 95% by weight of the particles have a diameter greater than 1$\mu$ and at least 90% by number of the particles have a diameter less than 6$\mu$.

The compositions in the form of dry powders preferably include a solid fine powder diluent and are conveniently presented in a pierceable capsule, for example of gelatin.

Self-propelling compositions of the invention may be either powder-dispensing compositions or compositions dispensing the active ingredient in the form of droplets of a solution or suspension. Self-propelling powder-dispensing compositions include a liquid porpellant having a boiling point of below 65° F at atmospheric pressure. Generally the propellant may constitute 50 to 99.9% w/w of the composition whilst the active ingredient may constitute 0.1 to 20% w/w, for example, about 2% w/w, of the composition. The carrier in such compositions may include other constituents, in particular a liquid non-ionic or solid anionic surfactant, or a solid diluent (preferably having a particle size of the same order as of the particles of active ingredient) or both. The surfactant may constitute up to 20% w/w, though preferably it constitutes below 1% w/w of the composition.

Self-propelling composition wherein the active ingredient is present in solution comprise an active ingredient, propellant and co-solvent, and advantageously an antioxidant stabiliser. The co-solvents may constitute 5 to 40% w/w of the composition, though preferably less than 20% w/w of the composition.

Compositions of the present invention may also be in the form of aqueous or dilute alcoholic solution, optionally a sterile solution, of the active ingredient for use in a nebuliser or atomiser.

Compositions of the present invention suitable for parenteral administration conveniently comprise sterile aqueous solutions of the active ingredient, which solutions are preferably isotonic with blood of a patient under treatment.

Pharmaceutical composition of the present invention suitable for topical use include compositions suitable for administration to the skin, eyes, nose and mouth. Compositions for use on the skin include lotions and creams comprising liquid or semi-solid emulsions, either oil-in-water or water-in-oil, and ointment, preferably containing from 0.2 to 5% w/v of the active ingredient. Desirably the creams and ointments should contain a preservative such as methyl hydroxybenzoate.

Compositions for administration to the eye include eye drops comprising the active ingredient in aqueous or oily solution and ointments, preferably containing 0.2 to 5% w/v of the active ingredient. The eye drops are desirably fungistatic and bacteriostatic and are preferably prepared sterile.

Compositions suitable for administration to the nose include powder, self-propelling and spray compositions similar to those already described under compositions suitable for pulmonary administration but having when dispersed, a somewhat larger particle size of the order of 10 to 200 microns. Other compositions suitable for nasal administration include a coarse powder having a particle size of 20 to 500 microns which is administered in the manner in which snuff is taken i.e. by rapid inhalation through the nasal passage from a container of the powder held close up to the nose. Another composition suitable for nasal administration is nasal drops comprising 0.2 to 5% w/v of the active ingredient in aqueous or oily solution.

Compositions suitable for topical administration in the mouth include lozenges comprising 10 to 100 mg. of the active ingredient in a flavoured base, usually sucrose and acacia or tragacanth; and pastilles comprising 10 to 100 mg. of the active ingredient in an inert base such as gelatin and glycerin; or sucrose and acacia.

Other therapeutic ingredients suitable for inclusion in the hereinbefore described compositions, especially in the case of those compositions intended for use in the treatment of allergic asthma, include bronchodilators such as isoprenaline, adrenaline, orciprenaline, isoethanine and physiologically acceptable acid addition salts thereof, espceially isoprenaline sulphate. Conveniently the bronchodilator is present in an amount of 0.1 to 50% w/w of the weight of active ingredient present.

Included within the scope of the present invention, but in no way limited thereto, are the following specific features:-

1. A compound of formula I as defined hereinabove, where novel.

2. The synthesis of compounds of formula I as defined hereinabove, by any method known in the art for preparing them and compounds of analogous chemical structure.

3. Pharmaceutical compositions comprising a compound of formula I as defined hereinabove in association with a pharmaceutically acceptable carrier therefor.

4. The preparation of pharmaceutical compositions comprising a compound of formula I as defined hereinabove as an active ingredient, by any conventional method, including admixture of the ingredients.

5. A method of treatment or prophylaxis of mammalian allergic conditions comprising administration of a therapeutic or prophylactic dose respectively, of a compound of formula I as defined hereinabove.

The following preparations and examples illustrate the methods for preparing compounds in accordance with the present invention, as well as compounds and compositions of the present invention. In the examples and preparations, all temperatures are in degrees Celsius. Where melting point are not given for compounds of formula I, the compounds decompose at temperatures below their melting points and/or their melting points are at temperatures above those readily determinable by conventional techniques. In these preparations and examples, the numbering of substituent positions in the tricyclic nucleus used is not necessarily the same as that used in formula I, but is the standard numbering in respect of the particular tricyclic nucleus concerned, as given in the "Ring Index", IInd Edition, published by the American Chemical Society, 1960. This standard numbering also applies in respect of the individual named compounds disclosed hereinbefore.

Reference Preparation 1- Preparation of cis- and trans-2-carboxythianthrene-5,10-dioxide A. Preparation of Thianthrene-2-carboxylic acid Acetic anhydride (22.4 g) in dichloroethane (75 ml) was added to a suspension of aluminium chloride (58.4 g) in dichloroethane (100 ml) at 0° C. This was then added to a solution of thianthrene (43.2 g) in dichloroethane (600 ml) at 0° C. The reaction mixture was stirred for 1 hour at 0° C, then allowed to warm to room temperature and poured onto ice and concentrated hydrochloric acid. The organic layer was separated and the aqueous extracted with dichloroethane. The combined extracts were washed, dried and evaporated to give a brown oily product of crude 2-acetylthianthrene. This was heated to 90° C. for 2.5 hours with sodium hypochlorite solution (containing 14% available chlorine) (270 ml), normal sodium hydroxide solution (600 ml) and 1,4 dioxan (600 ml). After standing for 16 hours fine needles were filtered from the reaction mixture. These were washed and dried to give thianthrene, m.pt. 155° C. The reaction liquors were poured onto ice and concentrated hydrochloric acid. The precipitated solid was filtered off, washed with water, and dissolved in 0.5 Normal sodium hydroxide solution. The mixture was filtered from some insoluble material, and the alkaline filtrates re-acidified with concentrated hydrochloric acid. The precipitated solid was washed with water, and dried in vacuo to yield thianthrene-2-carboxylic acid, m.pt. ca. 220° C. Recrystallisation from glacial acetic acid and acetonitrile raised the melting point to 227°–8° C.

Found: %C, 59.60; %H, 3.19; %N, Nil. $C_{13}H_8O_2S_2$ requires %C, 60.01; %H, 3.10; %N, Nil.

B. Preparation of cis- and trans-2-carboxythianthrene-5,10-dioxide

Thianthrene-2-carboxylic acid (26.0 g) was suspended in glacial acetic acid (300 ml) and 30% hydrogen peroxide (45.3 g) was added at room temperature. The reaction was left to stand for 68 hours. The precipitated solid was filtered off, washed, dried and recrystallised from glacial acetic acid to give a mixture of products melting between 240° and 290° C. This was warmed with 0.1 Normal potassium hydroxide solution (550 ml), filtering whilst hot from some insoluble material. The hot alkaline filtrates were acidified with warm Normal hydrochloric acid (14 ml) and filtered whilst hot. The remaining liquors were heated nearly to boiling and acidified with hot, Normal hydrochloric acid (39 ml). The precipitated solid was filtered, washed and dried to yield trans-2-carboxythianthrene-5,10-dioxide (monohydrate) m.pt. 245°–8° C. Recrystallisation from glacial acetic acid raised the melting point to 248°–9° C.

Found: %C, 50.56; %H, 3.12; %N, Nil. $C_{13}H_{10}O_5S_2$ requires %C, 60.33; %H, 3.25; %N, Nil. Trans-2-carboxythianthrene-5,10-dioxide (monohydrate) (2.0 g) was heated to 280° C. for 30 minutes. The resulting solid was dried to yield cis-2-carboxythianthrene-5,10-dioxide, m.pt. 300°–1° C. Recrystallisation from dimethylformamide raised the melting point to 301°–2° C.

Found: %C, 53.44; %H, 2.76; %N, Nil. $C_{13}H_8O_4S_2$ requires %C, 53.62; %H, 2.81; %N, Nil.

EXAMPLE 1

Preparation of 2,8-Dicarboxyphenoxathiin-10-dioxide.

A. Preparation of 2,8-Diacetylphenoxathiin

Aluminum chloride (102.5 g) was added portionwise to a stirred solution of phenoxathiin (51.5 g) and acetyl chloride (66 g) in carbon disulphide (425 ml) over a period of 3 hours. The mixture was poured on to ice and hydrochloric acid and the precipitated solid filtered off, washed with water and dried. Trituration with warm acetone removed mono-acetylated product, and the residual product was filtered off and recrystallised from dioxan, m.p. 179° C.

B. Preparation of 2,8-dicarboxyphenoxathiin-10-oxide 2,8-Diacetylphenoxathiin (9.94 g) was stirred in acetic acid (105 ml) while 35% w/v nitric acid (17.5 ml) was added in drops. The mixture was boiled under reflux for 2 hours cooled, and poured on to ice. The precipitated product was filtered off and dried to give crude product which was recrystallised from aqueous dimethylsulphoxide and then dimethylformamide, to give purified product m.p. above 460° C.

Found: C 55.01%, H 2.80%, S 10.30%. $C_{14}H_8O_6S$ requires C 55.27%, H 2.65%, S 10.53%.

EXAMPLE 2

Preparation of 2-carboxyphenoxathiin-10-oxide

A. Preparation of 2-Acetylphenoxathiin

Phenoxathiin (22.9 g) and acetyl chloride (8.8 ml) were dissolved in carbon disulphide (120 ml) and mechanically stirred while aluminium chloride (15.5 g) was added in small portions. The red mixture was stirred for 2 hr. at room temperature, then boiled under reflux on the water bath for a further 2¼ hours. The mixture was cooled and poured on to a mixture of ice and hydrochloric acid, and the precipitated product filtered off, washed with water, and recrystallised once from ethanol and twice from petroleum ether (b.p. 80°–100° C), m.p. 112° C.

B. Preparation of Phenoxathiin-2-carboxylic acid

A mixture of 2-acetylphenoxathiin (4.80 g), sodium hypochlorite solution (95 ml.; 5.7% available chlorine), 4% w/v sodium hydroxide solution (100 ml) and dioxan (100 ml) was mechanically stirred on the steam bath for 5 hr. The solution was poured on to ice and excess hydrochloric acid with stirring. The white precipitate was filtered off and dissolved in hot 4% w/v sodium hydroxide solution (40 ml) and filtered. The sodium salt of the required acid crystallised from the filtrate on cooling and was filtered off, dissolved in boiling water, and the acid precipitated by addition of excess hydrochloric acid. It was filtered off and recrystallised from acetic acid, m.p. 253° C.

C. Preparation of 2-carboxyphenoxathiin-10-oxide

Phenoxathiin-2-carboxylic acid (0.61g) was dissolved in refluxing absolute ethanol (40 ml) and 30% w/v hydrogen peroxide solution (1.50 ml) added. Reflux was maintained for 2 hours, more 30% w/v hydrogen peroxide solution (1.00 ml.) added, and reflux continued for 17 hours. The solution was evaporated to low volume, and the product crystallised out. The solid was filtered, washed and dried to give 2-carboxyphenoxathiin-10-oxide m.p. 223° C. Recrystallisation from absolute ethanol raised the melting point to 237° C.

$C_{13}H_8O_4S$ requires %C,59.99; %H,3.09; %S,12.31; Found %C,59.88; %H,3.06; %S,12.34.

EXAMPLE 3

Preparation of 3-carboxythioxanthone-10-oxide

Thioxanthone-3-carboxylic acid (0.51g) and iodosobenzene diacetate (0.64g) were refluxed in glacial acetic acid (20 ml.) for 1.5 hours. More iodosobenzene diacetate (0.32g) was added and reflux continued for a further 4.5 hours. The reaction solution deposited crystals, on cooling, which were filtered, washed and dried to give 3-carboxythioxanthone-10-oxide, m.p. 295°-6° C. Recrystallisation from glacial acetic acid did not raise the melting point.

$C_{14}H_8O_4S$ requires %C,61.76; %H,2.96; Found %C,61.87; %H,3.06.

EXAMPLE 4

Preparation of 2-(5-Tetrazolyl)phenoxathiin-10-oxide

A. Preparation of 2-cyanophenoxathiin

Phenoxathiin-2-carboxylic acid (10.95g) was refluxed for 2 hours with thionyl chloride (100 ml.). The resulting solution was evaporated to give the corresponding acid chloride as an oil. This was added to .880 ammonium hydroxide with stirring and ice-cooling to yield crude 2-amidophenoxathiin. This was then added to a solution of thionyl chloride (15 ml.) and dimethylformamide (105 ml.) at −20° C, and stirred at this temperature for a further 2 hours. The reaction solution was poured onto water, the solid being filtered and dried to give crude 2-cyanophenoxathiin. This was purified by column chromatography, using neutral alumina, to give 2-cyanophenoxathiin m.p. 107°-112° C. Recrystallisation from ethanol raised the melting point to 118°-120° C.

B. Preparation of 2-(5-tetrazolyl)phenoxathiin 2-cyanophenoxathiin (2.25g), sodium azide (0.68g) ammonium chloride (0.59g) and dimethylformamide (30 ml.) were heated for 9 hours at 130° C. The solution was poured onto ice and 2 Normal sodium hydroxide solution, and extracted with chloroform. The aqueous phase was acidified with concentrated hydrochloric acid. The solid was filtered, washed and dried to give 2-5-tetrazolyl)phenoxathiin m.p. 210°-2° C. Recrystallisation from glacial acetic acid raised the melting point to 220°-1° C.

C. Preparation of 2-(5-tetrazolyl)phenoxathiin-10-oxide 2-(5-Tetrazolyl)phenoxathiin (0.70g) and m-chloroperoxybenzoic acid (0.45g) were stirred for 2 hours at room temperature in acetone (20 ml.) and water (5 ml.). The reaction mixture was diluted with water, and the solid filtered, dried, washed with ether and re-dried to give 2-(5-tetrazolyl)phenoxathiin-10-oxide m.p. 267°-8° C. Recrystallisation from glacial acetic acid raised the melting point to 280°-1° C.

$C_{13}H_8N_4O_2S$ requires %C,54.93; %H,2.84; %N,19.71; Found %C,54.09; %H,2.75; %N,19.64.

EXAMPLE 5

Preparation of 3-(5-tetrazolyl)thianthrene-5-oxide

Trans-2-carboxythianthrene-5,10-dioxide (of Reference Preparation 1) (2.5g) was refluxed for 1 hour with thionyl chloride (50 ml.). The resulting solution was evaporated to dryness to give the acid chloride as a yellow oil. This was added to .880 ammonium hydroxide solution (100 ml.), with ice-cooling and stirring. The crude amide was fitered off, washed with water, dried at 90° C. then added to a stirred mixture of thionyl chloride (5 ml.) and dimethylformamide (35 ml.) at −20° C. The reaction mixture was stirred for 1 hour at −10° C, poured onto ice-water, and the precipitated solid filtered, washed, and dried in vacuo at 80° C. to yield the crude nitrile, m.p. 104°-8° C. This was then reacted with sodium azide (0.45 g), ammonium chloride (0.038 g) and dimethylformamide (20 ml.) for 7 hours at 130° C. The reaction solution was poured onto 2 Normal sodium hydroxide solution and extracted with chloroform. The aqueous phase was acidified with concentrated hydrochloric acid and the precipitated solid filtered off, washed, and dried in vacuo at 80° C. to yield 3-(5-tetrazolyl)thianthrene-5-oxide m.p. 200°-4° C. Recrystallisation from glacial acetic acid raised the melting point to 208°-211° C.

$C_{13}H_8N_4OS_2$ requires %C: 52.00, %H: 2.69; %N: 18.66; Microanalysis found %C: 51.77; %H, 2,49; %N: 18.44. N.B. The position of the sulphoxide linkage relative to the tetrazolyl substituent has been tentatively assigned on the basis of Nuclear Magnetic Resonance studies which favoured the structure given hereinabove in preference to the structure: 3-(5-tetrazolyl)thianthrene-10-oxide.

EXAMPLE 6

Preparation of 7-chloro-3-(5-tetrazolyl)thioxanthene-10-oxide

A. Preparation of p-Chlorophenylthioterephthalic acid p-Chlorophenylthioterephthalonitrile (8.0g.), sodium hydroxide (4.55g) and water (150 ml.) were boiled together under reflux for 16 hr. Filtration removed an insoluble residue of p-chlorophenylthioterephthalic diamide, m.pt. 308°-310° C. Acidification of the filtrate with hydrochloric acid yielded p-chlorophenylthioterephthalic acid, m.pt. 346°-347° C. A sample recrystallised from acetic acid melted at 353°-354° C.

B. Preparation of 7-Chlorothioxanthone-3-carboxylic acid p-Chlorophenylthioterephthalic acid (9.10g.) was heated with sulphuric acid (125 ml.) at 110° C. for 2 hr. The mixture was poured into water and the yellow product filtered off, washed with water, and dried, yielding 7-chlorothioxanthone-3-carboxylic acid. A sample recrystallised from dimethylformamide melted with sublimation of 365° C.

Found C, 58.14%; H, 2,56%. $C_{14}H_7ClO_3S$ requires C, 57.84%; H, 2.43%.

C. Preparation of 7-Chlorothioxanthene-3-carboxylic acid

7-Chlorothioxanthone-3-carboxylic acid (6.0g.), red phosphorus (6.0g.) 60% hydriodic acid (20 ml.) and acetic acid (90 ml.) were boiled together under reflux for 65 hr. The cooled reaction mixture was diluted with water and the solid material filtered off and recrystallised from acetic acid, filtering off an insoluble residue, to yield 7-chlorothioxanthene-3-carboxylic acid (1.95g.), m.pt. 294°–295° C.

D. Preparation of 2-Chloro-6-cyanothioxanthene

7-Chlorothioxanthene-3-carboxylic acid (1.90g.), methylene chloride (50 ml.), thionyl chloride (2.0 ml.) and dimethylformamide (1 drop) were boiled together under reflux for 3 hr. Evaporation of the resulting solution yielded the crude acid chloride, which was redissolved in methylene chloride (50 ml.) and poured into iced 0.880 ammonia (30 ml.). Evaporation of the organic solvent and filtration gave the solid amide, which was filtered off and dried. The amide was suspended in dimethylformamide (20 ml.) and the mixture was cooled to −40° C. Thionyl chloride (2.0 ml.) was added and the mixture stored at 0° C. for 1 hr. After dilution with water 2-chloro-6-cyanothioxanthone was filtered off and recrystallised from acetic acid, m.pt. 165°–166° C.

E. Preparation of 7-Chloro-3(5-tetrazolyl)thioxanthene

A mixture of 2-chloro-6-cyanothioxanthene (1.38g.), sodium azide (0.71g.), ammonium chloride (0.59g.) and dimethylformamide (20 ml.) was heated at 130° C. for 7 hr. The mixture was cooled, poured into cold dilute hydrochloric acid, and the precipitated product filtered off. Recrystallisation from acetic acid yielded 7-chloro-3(5-tetrazolyl)thioxanthene, which was dired at 154° C./20mm Hg., m.pt. 257° C. with decomposition.

Found: C,55.95%; H,2.98%, N,18.99%. $C_{14}H_9ClN_4S$; requires C,55.90%, H,3.02%; N,18.63%.

F. Preparation of 7-Chloro-3(5-tetrazolyl)thioxanthene-10-oxide

7-Chloro-3(5-tetrazolyl)thioxanthene (100g.) was suspended in a mixture of acetone (40 ml.) and water (10 ml.) and 85% m-chloroperoxybenzoic acid (0.61g.) was added in portions. After 1.5 hr. stirring at 25° C. the mixture was diluted with water and allowed to stand overnight. The solid product was filtered off and dried, then boiled under refulx with ether (50 ml.), filtered, washed with ether, and dried, yielding 7-chloro-3(5-tetrazolyl)thioxanthene-10-oxide which had no defined melting point.

Found: C,52.89%; H,2.84%; N,17.50%; $C_{14}H_9ClN_4OS$; requires C,53.09%; H,2.86%; N,17.68%.

EXAMPLE 7

Preparation of Sodium salt of 2,8-dicarboxyphenoxathiin-10-oxide

Sodium salt of 2,8-dicarboxyphenoxathiin-10-oxide 2,8-dicarboxyphenoxathiin (0.304g.) (of Example 1) was dissolved in 0.1 Normal sodium hydroxide (20.0 ml.) at 25° C. A small solid residue was filtered off, and the filtrate evaporated to dryness. The residual sodium salt was dried at room temperature in vacuo, and contained ca. 12% water of crystallisation, as shown by microanalysis.

Found: C,42.22%; H,2.70%. 88% $C_{14}H_6Na_2O_6S$ + 12% $H_2O$; requires C,42.24%; H,2.85%.

EXAMPLE A — POWDER CAPSULES FOR INHALATION

| | |
|---|---|
| 3-Carboxythioxanthone-10-oxide sodium salt (0.5–7.0 μm powder) | 4 mg |
| Lactose (30–90 μm powder) | 46.0 mg |

The powders were mixed until homogeneous and filled into suitably sized hard gelatin capsules, 50 mg of mixture per capsule.

EXAMPLE B — INJECTION SOLUTION

| | |
|---|---|
| 3-Carboxythioxanthone-10-oxide sodium salt | 50 mg |
| Water for Injections B.P. to | 5.0 ml |

The sodium salt was dissolved in 95% of the water and then made up to volume and sterilised by filtration: The resulting solution was distributed into ampoules under aseptic conditions.

EXAMPLE C — INHALATION AEROSOL

| | |
|---|---|
| 3-Carboxythioxanthone-10-oxide (0.5–7.0 μm powder) | 200 mg |
| Sorbitan Trioleate | 100 mg |
| Saccharin Sodium (0.5–7.0 μm powder) | 5 mg |
| Menthol | 2 mg |
| Trichlorotrifluoromethane | 4.5 g |
| Dichlorodifluoromethane to | 10.0 ml |

The Sorbitan Trioleate and Menthol were dissolved in the Trichlorofluoromethane. The Saccharin Sodium and Carboxylic acid were dispersed in the mixture which was then transferred to a suitable aerosol canister and the Dichlorofluoromethane injected through the valve system. This composition provides 2 mg. of Acid in each 100 μl. dose.

What we claim is:

1. A method for the treatment or prophylaxis of an allergic condition selected from the group consisting of asthma, hay fever, conjunctivitis, urticaria and eczema of a mammal comprising administration to the mammal in need thereof of a therapeutically or prophylactically effective antiallergic dose of a tricyclic compound of formula I

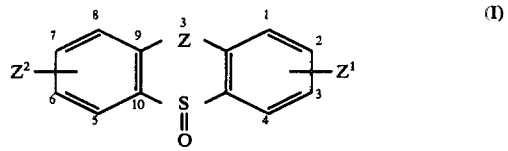

wherein $Z^1$ is carboxyl in the 1-, 2-, 3-, or 4-position $Z^2$ is hydrogen or a substituent in the 5-, 6-, 7-, or 8- position selected from the group consisting of carboxyl, alkylsulphonyl, alkylsulphinyl, thioalkyl, amino, acylamino, nitro, cyano, halogen, acyl, alkyl and alkoxy wherein the "alkyl" moiety of each of the acyl, alkyl, alkoxy, thioalkyl, acylamino, alkylsulphinyl and alkylsulphonyl groups has 1 to 6 carbon atoms; and $Z^3$ is sulphur or sulphoxide;

a pharmaceutically acceptable salt thereof or when at least one of $Z^1$ and $Z^2$ is a carboxyl group, an alkyl ester, unsubstituted amide, N-alkylamide or N, N-dialkylamide wherein "alkyl" has 1 to 6 carbon atoms, thereof.

2. A method as claimed in claim 1 wherein administration is effected by the pulmonary route as a powder having a particle size in the range of 0.5 to 7μ.

3. A method as claimed in claim 2 wherein the tricyclic compound is administered at a dose of 20 μg. to 0.5 mg. per kilogram bodyweight of said mammal.

4. A method as claimed in claim 1 wherein administration is effected by the oral route.

5. A method as claimed in claim 4 wherein the tricyclic compound is administered at a dose of 1 to 50 mg. per kilogram bodyweight of said mammal.

6. A method as claimed in claim 1 wherein said allergic condition is allergic asthma.

7. The method of claim 1 in which halogen is chlorine or bromine.

* * * * *